Figure 1:
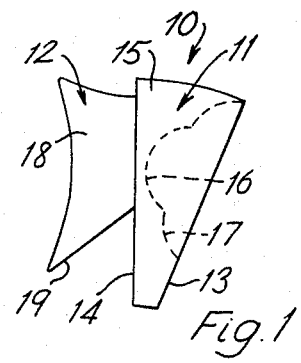
Figure 3:
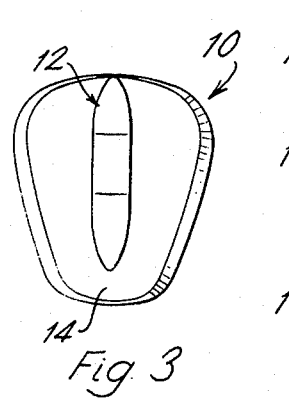
Figure 2:
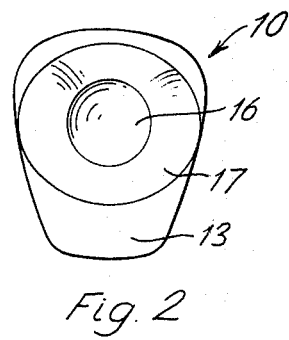
Figure 4:
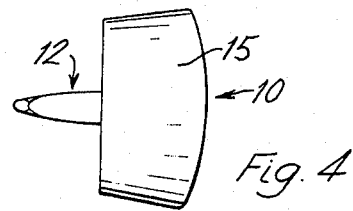

United States Patent [19]

Scales

[11] 4,106,130
[45] Aug. 15, 1978

[54] ENDOPROSTHETIC BONE JOINT DEVICES

[75] Inventor: John Tracy Scales, Stanmore, England

[73] Assignee: National Research Development Corporation, London, England

[21] Appl. No.: 767,949

[22] Filed: Feb. 11, 1977

[30] Foreign Application Priority Data

Feb. 20, 1976 [GB] United Kingdom ................. 6803/76

[51] Int. Cl.² .............................................. A61F 1/24
[52] U.S. Cl. ........................................ 3/1.91; 3/1.912; 128/92 C
[58] Field of Search .................................. 3/1.9–1.913, 3/1; 128/92 C, 92 CA

[56] References Cited

U.S. PATENT DOCUMENTS

| 3,584,318 | 6/1971 | Scales et al. | 3/1.91 |
| 3,694,821 | 10/1972 | Moritz | 3/1.911 |
| 3,922,726 | 12/1975 | Trentani et al. | 3/1.912 |
| 4,001,897 | 1/1977 | Rambert et al. | 3/1.913 |
| 4,024,588 | 5/1977 | Janssen et al. | 3/1.91 |

FOREIGN PATENT DOCUMENTS 2,400,650 7/1974 Fed. Rep. of Germany ............. 3/1.91

*Primary Examiner*—Ronald L. Frinks
*Attorney, Agent, or Firm*—Cushman, Darby & Cushman

[57] ABSTRACT

An endoprosthetic bone joint device of ball-and-socket form has a socket component with a compound concave surface therein including a cup bounded by an annular trough, the co-operating ball normally seating in the cup but being alternatively seatable in the trough when dislocation would otherwise occur.

9 Claims, 6 Drawing Figures

ENDOPROSTHETIC BONE JOINT DEVICES

This invention concerns prosthetic devices, and more particularly endoprosthetic bone joint devices. In fact the invention has been developed initially for application to the shoulder joint, but is considered applicable to other joints as will be appreciated hereinafter.

The natural shoulder joint is generally of ball-and-socket form but with relatively incongruous bearing components. The ball is provided by the humeral head which normally closely approximates to spherical shaping, and the socket is provided by the scapular glenoid cavity which is of elongate shallow dished shape with significantly less curvature than the humeral head. This natural assembly affords a large range of articulation and allows movement of the centre of rotation, while being stabilized controlled by the ligaments and musculature of the surrounding capsule.

Endoprosthetic shoulder joint devices as so far proposed and used in clinical practice invariably seek to simulate the natural joint by use of a simplified assembly of complementary spherically shaped ball-and-socket components. While these devices have proved useful in providing a viable and advantageous surgical option in respect of some conditions, the devices can be regarded as open to improvement. One factor giving rise to this view is that each such device has a single centre of rotation and for a given joint which is to be replaced there will accordingly be a single location for this centre to attain the optimum compability with the relevant bones and capsule. It follows that the surgeon must seek to achieve this optimum location in order to minimized the risk of possible disadvantageous consequences which can otherwise occur. These consequences can involve a limited range of articulation relative to that which the device is designed to allow, dislocation of the device, and mechanical failure of the device such as loosening of its securement with the bones.

An object of the present invention is to provide an improved endoprosthetic bone joint device which reduces the risk of such consequences arising. To this end the invention provides a device comprising two components respectively adapted for securement to different bones of the relevant joint, and respectively including male and female bearing parts for mutual articulatory engagement, the male part having a rounded convex bearing surface, the female part having a compound concave bearing surface including a cupped area bounded by an annular troughed area, and the curvature of said cupped area and the transverse curvature of said troughed area each being no greater than the curvature of said convex surface.

It is presently preferred that the convex surface and the cupped area are spherically shaped, and that the troughed area is circularly shaped in transverse cross-section, with the radii of such shapings being substantially equal.

However, this is not essential and the last two curvatures, and particularly that of the cupped area, may be less then that of the convex surface to more closely simulate lack of congruity in the corresponding natural joint. Similarly, the cupped area may be of elongated form in application to the shoulder joint. These possibilities are of particular relevance to a situation where the likelihood of dislocation is reduced by the provision of prosthetic ligamentous or other capsular elements.

Also, in application to a shoulder joint it is presently preferred that the components with the male and female bearing parts be respectively associated with the humerus and scapula, and that the securement adaptation be generally in accordance with U.S. Pat.No. 3,694,820. Again, this is not essential since a so-called reverse anatomical configuration is possible, as is different securement adaption.

Advantage in use of the present invention stems from the compound concave surface of which the cupped area is intended to serve as a primary, normally-engaged bearing surface relative to the male bearing part, while the troughed area serves as a secondary surface with which the male bearing part can be engaged for continued articulation in circumstances when a prior device can inhibit articulation, dislocate, or unduly stress the component securement.

Figure 6:
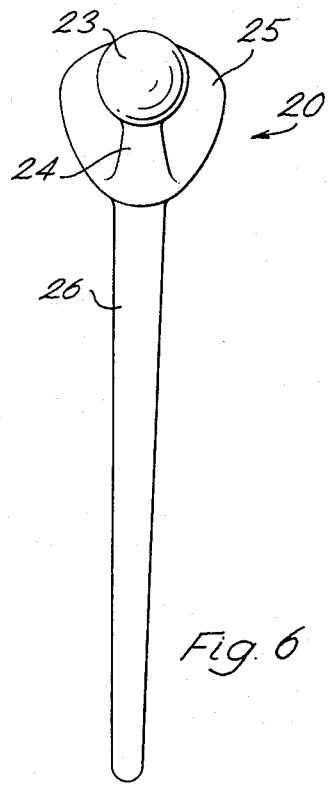
Figure 5:
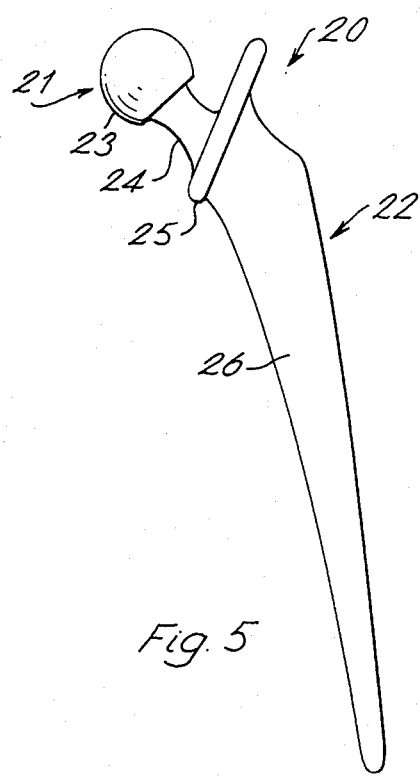

In order that the invention may be more fully understood, the same will now be described, by way of example, with reference to the accompanying drawings, in which:

FIGS. 1 to 4 are respective side, front, rear, and plan views of a scapular component of a shoulder joint device according to the invention; and FIGS. 5 and 6 are respective front and side views of an associated humeral component.

The illustrated scapular component is denoted generally at 10 and is of unitary construction of plastics material comprising a bearing part 11 and a securement part 12. The bearing part is symmetrical and is conveniently regarded as a generally frustoconical body formed with an inclined face 13 opposite to its base 14 so that its curved surface 15 is generally triangular in opposed side views, and in which the inclined face is dished. This dishing provides a compound concave bearing surface having a cupped area 16 bounded by an annular troughed area 17. The cupped area is spherically shaped and is of minor segmental extent, suitably of about one third of a sphere. The troughed area has circular arcuate cross-sectional shape with the same curvature as, but less extent than, that of the cupped area; the latter area is more deeply located in the bearing part relative to the inclined face than the former area; and the mouth of the former area is convergently inclined in conical manner relative to the mouth of the latter.

The securement part 12 is in the form of a web 18 extending from the base of the bearing part. This web is disposed in the medial plane of symmetry of the frustoconcial shape of the bearing part, but is itself non-symmetrical in side view since it extends further, in a radial direction from the bearing part relative to the cupped area, at its edge 19 nearer the narrower side of the bearing part than elsewhere. This web shape and location in fact accords with the afore-mentioned U.S. Pat. No. 3,694,820.

The illustrated humeral component is denoted generally at 20 and is of unitary metal construction comprising a bearing part 21 and a securement part 22. The bearing part consists of a spherically-shaped ball 23 connected through a neck portion 24 and flange 25 to the wider end of a tapered elongate stem 26, the stem forming the securement part.

In use of the illustrated device the components are secured in similar manner to that described in the afore-mentioned U.S. Pat. No. 3,694,820 and so that the head 23 is normally in mutual articulatory engagement with the cupped area 16. In this normal engagement the device functions similarly to the prior devices of simple ball-and socket form. However, it will be appreciated that the present device differs by way of the troughed secondary bearing surface area into which, as noted above, the head can rock for continued articulatory engagement under conditions which can otherwise give rise to undersirable consequences with a prior device.

While the invention has been described with more particular reference to the illustrated example, it is not intended that the invention can be construed as limited thereby. Thus, it has been noted that the invention can be applied to joints other than the shoulder, and it is clear that other joints of ball-and-socket form, such as the hip, are relevant in this context. Also, yet other joints are of relevance and continuing development of the invention involves an elbow joint device.

I claim:

1. An endoprosthetic bone joint device comprising two components respectively adapted for securement to different bones of the relevant joint, and respectively including male and female bearing parts in mutual articulatory engagement, the male part having a rounded convex bearing surface, the female part having a compound concave bearing surface including a cupped area bounded by an annular troughed area, and the curvature of said cupped area and the transverse curvature of said troughed area each being no greater than the curvature of said convex surface.

2. A device according to claim 1 wherein said convex surface is spherically shaped.

3. A device according to claim 2 wherein said cupped area is spherically shaped and said troughed area is circularly shaped in transverse cross-section, the radii of such shapings being substantially equal to that of said convex bearing surface.

4. A device according to claim 1 wherein said cupped area is more deeply located than said troughed area in said female bearing part.

5. A device according to claim 4 wherein the mouth of said troughed area is convergently inclined in conical manner relative to said cupped area.

6. A device according to claim 1 wherein said cupped area is of greater arcuate extent than said troughed area in a common transverse cross-section.

7. A device according to claim 3 wherein said cupped area is more deeply located than said troughed area in said female bearing part, wherein the mouth of said troughed area is convergently inclined in crucial manner relative to said cupped area, and wherein said cupped area is of a greater arcuate extent than said troughed area in a common transverse cross-section.

8. An endoprosthetic shoulder joint device according to claim 7 claim wherein said components having said male and female bearing parts respectively serve as humeral and scapular components, wherein said female bearing part is in the general form of a symmetrical frusto-conical body having an inclined face opposite to its base, said inclined face being dished to define said concave surface, and wherein said female bearing part is adapted for securement to the scapula by the provision of a member projecting therefrom in the medial plane of said body.

9. For use in an endoprosthetic bone joint device of ball-and-socket form, a socket component having a compound concave surface including a cupped area bounded by an annular troughed area.

* * * * *